United States Patent
Yan et al.

(10) Patent No.: US 6,596,321 B1
(45) Date of Patent: Jul. 22, 2003

(54) PHARMACEUTICAL COMPOSITION FOR TREATING ANGIOCARDIOPATHY AND THE METHOD OF PRODUCING THEREOF

(75) Inventors: Yongqing Yan, Nanjing (CN); Minghui Tang, Nanjing (CN); Danni Zhu, Nanjing (CN); Shufei Zhuang, Nanjing (CN)

(73) Assignees: China Pharmaceutical University, Nanjing (CN); Ningbo Asia-Pacific Biotechnology Ltd., Nangbo (CN)

( * ) Notice: Subject to any disclaimer, the term of this patent is extended or adjusted under 35 U.S.C. 154(b) by 0 days.

(21) Appl. No.: 09/936,171

(22) PCT Filed: Mar. 9, 2000

(86) PCT No.: PCT/CN00/00044

§ 371 (c)(1),
(2), (4) Date: Dec. 19, 2001

(87) PCT Pub. No.: WO00/53204

PCT Pub. Date: Sep. 14, 2000

(30) Foreign Application Priority Data

Mar. 9, 1999 (CN) ........................................ 991140915 A

(51) Int. Cl.⁷ ................................................. A61K 35/78
(52) U.S. Cl. ........................ 424/725; 424/728; 424/773; 424/777

(58) Field of Search ................................. 424/725, 728, 424/773, 777

(56) References Cited

U.S. PATENT DOCUMENTS 4,684,628 A * 8/1987 Liu

* cited by examiner

*Primary Examiner*—Leon B. Lankford, Jr.
*Assistant Examiner*—Susan D. Coe
(74) *Attorney, Agent, or Firm*—Crowell & Moring LLP

(57) ABSTRACT

This invention relates to a pharmaceutical composition used for treating cardiovascular diseases and a method for preparing it. The pharmaceutical composition mainly contains polysacchrides, saponins and amino acids extracted from Radix ginseng, Radix ophiopogonis and Fructus schisandrae chinensis. The method of preparing it includes the following steps: Radix ginseng, Radix ophiopogonis and Fructus schisandrae chinensis are decocted together in water; water extract or eluate is precipitated with alcohol or acetone, treated with macroporous adsorption resin and with ion exchange resin, and then separated to obtain pharmaceutical composition containing effective fractions of polysacchrides, saponins and amino acids. The above mentioned pharmaceutical composition can be formed into various preparations by mixing with any pharmaceutically acceptable auxiliary materials.

9 Claims, No Drawings

PHARMACEUTICAL COMPOSITION FOR TREATING ANGIOCARDIOPATHY AND THE METHOD OF PRODUCING THEREOF

TECHNICAL FIELD

This invention relates to a pharmaceutical composition for treatment of cardiovascular diseases and the method for preparing it. More particularly, it relates to a pharmaceutical composition Huxinkang comprising effective fractions of Complex ShengMaiSan (SMS), a Chinese traditional medicine.

BACKGROUND OF INVENTION

The cardiovascular diseases are common and occur frequently. They are the second diseases, the fatality rate of which is just only next to malignant tumors. Although there has been great improvement in respect of prevention and treatment for cardiovascular diseases, among them myocarditis and myocardosis, especially viral myocarditis, still lack effective medicine for treatment. At present, clinically only means of providing nutrition, coenzyme support and letting patients to take good rest are used. ShengMaiSan is an ancient prescription containing three Chinese traditional medicines of Radix ginseng, Radix ophiopogonis and Fructus schisandrae chinensis, and has been clinically used to treat cardiovascular diseases. The preparation of ShengMai-San currently is in the form of injection, granule, bags and oral liquid. The methods for preparing it can be divided into three kinds, namely, extracting the 3 medicines separately and then mixing the extractions; decocting the 3 medicines together; and combination of the above two methods. Please refer to Chinese Application for Patent for Invention No. 971071192.6. These methods play significant role in reforming preparations of SMS. However, components of Chinese traditional medicines are complicated, and complex preparations are even more complicated. For example, there are over 10 kinds of components just in Radix ginseng, such as saponins, proteins, polypeptides, amino acids, saccharides, organic acids, alkaloids, terpines, benzedrines, alkynes, lipids, volatile oils, etc. For existing SMS preparation, because the structural kinds of effective fractions are not determined, it is difficult to prepare drugs having definite kinds of main components. Only when kinds of main components are defined, reliable quality standards can be set up. When there are quality standards, stable clinic therapeutic effectiveness can be assured. Only if the quality of products is high, they will be accepted in international market. Therefore, important factors for Chinese traditional medicine to enter international market do not lie in that it has been made in apparently modem forms, such as injection, granule, bags and oral liquid, but in whether the modern forms have definite kinds of main components, whether clinic therapeutic effects of the drugs are stable, and whether there are definite quality standards.

The object of this invention is to provide a pharmaceutical composition for treatment of cardiovascular diseases, especially for viral myocarditis and expansile myocardosis. The composition has definite kinds of main components of Chinese traditional medicines.

The further object of this invention is to provide a pharmaceutical composition having definite kinds of main components, reduced dosage, better purity and quality, stable clinic therapeutic effects, and definite quality standards. The composition has effective fractions of the Chinese traditional medicines.

The further object of this invention is to provide a method to prepare the pharmaceutical composition by decocting the herbs together and then extracting different effective fractions.

The further object of this invention is to provide a method to prepare a pharmaceutical composition according to the combination of properties of the three medicines in Chinese ancient prescription of SMS, and molecular weights of active substances. The pharmaceutical composition has effective fractions of the three Chinese traditional medicines with definite kinds of main components.

BRIEF DESCRIPTION OF INVENTION

The technical solution of this invention is a pharmaceutical composition for treatment of cardiovascular diseases, which mainly contains polysaccharides, saponins and amino acids extracted from Radix ginseng, Radix ophiopogonis and Fructus schisandrae chinensis.

The above mentioned cardiovascular diseases mainly include viral myocarditis, expansile myocardosis, angina pectoris caused by coronary heart diseases, myocardial ischema, heart failure and arrhythmia.

The technical solution of this invention also includes a method to prepare the pharmaceutical composition for treatment of the above mentioned cardiovascular diseases. The method contains the following steps: Radix ginseng, Radix ophiopogonis and Fructus schisandrae chinensis are decocting together with water; water extract or eluate is precipitated by adding ethanol or acetone, treated with macroporous adsorption resin and then with ion exchange resin, and separated to obtain the pharmaceutical composition containing effective fractions of polysacchrides, saponins and amino-acids; and preparation is formed.

Particularly, the method for preparing the above mentioned pharmaceutical composition used for treating cardiovascular diseases contains the following steps:

Radix ginseng, Radix ophiopogonis and Fructus schisandrae chinensis in weight ratio of 1–5 1–3 1–3 are extracted with water;

after the water extract is concentrated, ethanol is added thereto so that the content of alcohol reaches 60%–80%;

polysacchrides are obtained by drying the ethanolic precipitate;

after ethanol is recovered the supernatant is treated with macroporous adsorption resin, first washed with de-ionized water until there is no sacchride, and then with 70%–80% ethanol until there is no saponin, and saponins are obtained from the recovered ethanolic eluate, wherein said macroporous adsorption resin can be D101, S-8 or D3520, among them D101 is preferred;

the water eluate is treated with cation exchange resin and eluated with 2%–15% arnmonia solution to obtain amino acids, wherein said cation exchange resin can be for example 732 cation exchange resin; and the polysacchrides, saponins and amino acids are mixed.

The water extract mentioned in the above method can also be placed on macroporous adsorption resin column after concentrated, here first washed with water and then with ethanol. The ethanol solution is recovered to obtain saponins. After concentrated the water eluate is precipitated by adding alcohol. Polysacchrides are obtained from the alcoholic precipitate. After alcohol being recovered the supernatant is placed on cation exchange resin column and washed with ammonia solution to obtain amino acids. Then the polysacchrides, saponins and amino acids are mixed.

The water extract mentioned in the above method can also be placed on cation exchange resin column, and first washed with water and then with ammonia solution. Amino acids are obtained from ammonia eluate. After concentrated the water eluate is placed on macroporous adsorption resin column and first washed with water and then with alcohol. Saponins are obtained from alcoholic eluate. After concentrated the water extract is precipitated by adding acetone to get polysacchrides. Then the polysacchrides, saponins and amino acids are mixed.

After the polysacchrides, saponins and amino acids are mixed, SMS extract is obtained. It can be mixed with any pharmaceutically acceptable auxiliary material to formulate into various forms, which can be fine granule, granule, capsule or tablet.

The separated effective fractions of polysacchrides, saponins and amino acids are determined qualitatively with conventional test reagents, for example, with anthrone reagent, thin-layer chromatography, and ninhydrin reagent respectively.

Yield range of effective fractions are: polysacchrides 2.77%–8.33%, saponins 1.29%–2.53%, and amino acids 1.04%–1.49%.

There are 20 kinds of amino acids in the obtained amino acids. The content of arginine is up to 5.029%. The contents of alanine, aspartic acid and γ-amino butyric acid are also high.

The main features of this invention lie in:
1. The pharmaceutical composition contains mainly polysacchrides, saponins and amino acids extracted from Radix ginseng, Radix ophiopogonis, and Fructus schisandrae chinensis. It is an effective medicine for treatment of cardiovascular diseases, especially viral myocarditis and expansile myocardosis.
2. This kind of pharmaceutical composition containing mainly polysacchrides, saponins and amino acids extracted from Radix ginseng, Radix ophiopogonis, and Fructus schisandrae chinensis has definite kinds of components and stable clinic therapeutic effects. It is easy to set up quality standards and to comply with requirements of international market.
3. This invention provides a preparation method, wherein a group of herbs are decocted together and then different effective fractions are extracted. "A group of herbs are decocted together" inherits theory and tradition of Chinese traditional medicine, and features of decoctum of Chinese traditional medicine are retained. "Different effective fractions are extracted" makes kinds of components clear, dosage reduced, and purity and quality improved.
4. The object of this invention also lies in that a pharmaceutical composition mainly comprising polysacchrides, saponins and amino acids is prepared according to the combination of three medicines in an ancient prescription SMS as well as molecular weight of active substances by using macroporous adsorption resin and cation exchange resin. Non-effective components such as mono-sacchrides, inorganic salts, pectin and resins are removed. Compared with the corresponding water decoctum, the dosage is reduced from 60% to 10% by weight of the raw herbs.
5. This invention proves for the first time that the polysacchrides, saponins and amino acids contained in Radix ginseng, Radix ophiopogonis, and Fructus schisandrae chinensis have protection effect to experiment animal model of viral myocarditis, which is accomplished by modulating immunity functions of organism. In addition, pharmacodynamic test shows that the comprehensive drug effects, when polysacchrides+saponins+amino acids are administered to patients jointly, are better than those when the three effective fractions are given separately. The effects are also better than when only two effective fractions of polysaccharides+saponins are administered jointly. Results observed under optic microscope show that SMT 22g/kg (by weight of raw herbs) significantly improve the pathologic change of myocardium caused by virus. Results observed under electronic microscope show that different parts of myocardium striped myofibril and appearance of mitochondria keep intact in the control group, while in the model group, damage to mitochondria is significant, having an appearance of absence. After part of mitochondria disappear, there are oviform void regions left. Muscular fiber was compressed and distorted due to swelling of mitochondria. Striped muscle tendon dissociated. While for the groups administered with the drug, the appearance of mitochondria is uniform, advantitia and spinal meninges systems can be seen clearly, and intact myofibril distributes evenly with every part being distinguished clearly. For the groups administered with SMS water decoct (SMS) or a mixture SMT of polysacchrides, saponins and amino acids, part of mitochondria have a shape of coacervation, and the damage is least. For the groups where polysacchrides, saponins and amino acids are administered separately, degree of damage is greater than the groups to which SMS and SMT are administered, with the phenomena of crista swelling of mitochondria, void regions in mitochondria and the likes occurring.

THE BEST WAY OF CARRYING OUT THE INVENTION

EXAMPLE 1

550 g of raw materials are weighed according to the proportions of Radix ginseng 1, Radix ophiopogonis 3, and Fructus schisandrae chinensis 1.5. 10 times of water is added to soak the materials for 30 minutes. The raw materials are extracted 3 times, each time being 60 minutes. The water extracts are combined, filtered and concentrated under reduced pressure to density of 1.04 (80° C.). 95% ethanol is added to make alcohol content reach 70% (20° C.). The mixture is kept still and filtered. The precipitation is sucked to dry and dried at 50° C. to get 41.2 g of polysacchrides. After ethanol is recovered the supematant is placed on macroporous adsorption resin column D101, and first washed with de-ionized water until there is no sacchride, then with 75% ethanol to the end. After ethanol is recovered the ethanolic eluate is dried to obtain 7.2 g of saponins. The water eluate is placed on cation exchange resin column, and washed with water to remove impurities and then with 5% ammonia solution to the end. The eluate is concentrated under reduced pressure and dried to get 7.79 g of amino acids. The polysacchrides, saponins and amino acids are blended, ground, passed through a screen of 60 mesh and mixed thoroughly. The pharmaceutical composition in form of fine granule is prepared by adding appropriate amount of auxiliary material thereto.

EXAMPLE 2

4 kg of raw materials are weighed according to the proportions of Radix ginseng 5, Radix ophiopogonis 3, and Fructus schisandrae chinensis 3. 10 times of water is added to soak the materials for 50 minutes. The raw materials are extracted 2 times, each time being 60 minutes. The water extracts are combined, placed on macroporous adsorption resin column (NKA-11) after concentrated, and first washed with water until there is no sacchride, then with 70% ethanol. Ethanol is recovered from the ethanolic eluate to get 52 g of saponins. After concentrated the water eluate is precipitated by adding acetone thereto. The precipitate is dried to obtain 131 g of polysacchrides. After acetone is recovered the supernatant is placed on cation exchange resin column and washed with water until there is no sacchride, and then with 10% ammonia solution with the water fraction being discarded. The ammonia fraction is dried under reduced pressure to get 42.6 g of amino acids.

EXAMPLE 3

1.2 kg of raw materials are weighed according to the proportions of Radix ginseng 1, Radix ophiopogonis 2, and Fructus schisandrae chinensis 1. 10 times of water is added to soak the materials for 20 minutes. The raw materials are extracted 4 times, each time being 30 minutes. The water extracts are combined and placed on cation exchange resin column, where first washed with water until there is no sacchride, then with 2% ammonia solution. 16.32 g of amino acids is obtained from the ammonia eluate. After concentrated the water eluate is placed on macroporous adsorption resin column (H-1 07), where first washed with de-ionized water until there is no sacchride, then with 80% ethanol. Ethanol is recovered from the ethanolic solution to obtain 17.64 g of saponins. After concentrated the water eluate is precipitate by adding ethanol to get 52.92 g of polysacchrides.

The extracted polysacchrides, saponins and amino acids are mixed to give SMS extract (SMT). SMT can be mixed with any pharmaceutically acceptable auxiliary material to formulate various preparations which may be in the form of fine granule, granule, capsule or tablet. The effective fractions of polysacchrides, saponins and amino acids can be determined by conventional qualitative reagents.

| Formulation of SMS in form of fine granule | SMT | 1250 g |
|---|---|---|
| | Lactose | 1000 g |
| | Microcrystalline cellulose | 243 g |
| | Aspartame | 7 g |

The material is packed as 1000 bags of fine granule preparation. Each bag contains 1.25 g of SMT.

EXAMPLE OF EXPERIMENT

The following example is an example where SMS is used for treatment of viral myocarditis.

We use mice model with viral myocarditis caused by Coxsackie virus $B_3$, wherein water decoctum of SMS (SMS) and SMS extract (SMT) are used as therapeutic drugs to evaluate the effects of SMS and SMT.

I. Materials and Method

1. Virus

Coxsackie virus B3, Nancy strain, propagated on human embryo kidney cell. Virus titer was determined in wish cells. The virus titer $TCID_{50}$ was $10^3$, and kept at −70° C.

2. Reagents

The test reagent kits LDH (Lactic Dehydrogenase), CK (Creatine Kinase), AST (Aspartate transferase) were provided by Jiansheng Institute of Bio-products; IL-2 radioimmuno-assay kit provided by Shanghai Institute of Atomic Energy; IFN-γ was measured with ELISA method, and the reagent kit was provided by Shenzhen Jingmei Bio-Engineering Company; Neutral red by Shanghai 3rd Reagents Factory; RMP1640 by GIBCO; TRI201 reagent by GIBCO, 1003511; diethyl pyrocarbonate (DEPC) by Amresco, E174-25G; Coxsackie virus gene enlarged kit by Fuhua Bio-Engineering Company; DNA marker by Promega Company and Huamei Bio-Engineering Company. The rest reagents are of AR made in China.

3. Instrument for the Experiment

Enzyme Binding Immunoassay instrument: DG3022A Model, Huadong Electronic Tube Factory.

Full automatic γ Counter: WIZARD1470 Model.

PCR Instrument: Perkin Elmer 9600 Model.

Gel automatic imaging system: Gel Doc 1000, Bio Rad.

4. Animals for the Experiment

BALB/c mice, male, 6–8 week age, provided by Experiment Animal Center of Nanjing University of Medical Sciences and General Hospital of Nanjing Military Region.

5. Method

BALB/c male mice were divided into groups randomly. For model group and test group: ip. $200TCIDVB_3$ 0.1 ml, for control group: ip. equal volume of physiological saline. At day 10, eyeballs were picked up to take blood sample, which was centrifuged at 3000rpm for 10 minutes. Serum was used to measure myocardium enzyme spectrum (CK, LDH, AST) level. The heart was weighed, and cut longitudinally. Half of it was soaked and fixed in 10% Formalin. The rest was soaked in 0.25% glutaraldehyde to be examined under electron microscope.

For test group, at the same time when ip virus was given, SMS 11g/kg, SMT 22g/kg (by weight of the raw medicine) and distilled water were administered orally.

II. Results of the Experiment

SMS 11g/kg and SMT 22g/kg (by weight of the raw medicine, and it is assumed from now on.) can significantly relieve the symptom of losing weight, and markedly lower the rising of myocardium enzyme spectrum CK, LDH, and AST (See Table 1).

SMT 22g/kg can significantly improve myocardium pathological change caused by virus. It can be observed from the electron microscope results that the appearances of different parts of myocardium striped myofibril and mitochondria kept intact in control group. For model group, damage to mitochondria was significant, showing absence, and after the disappearance of mitochondria, there were oviform void regions left. Muscle fiber was compressed and distorted after swelling of mitochondria, and striped muscle tendon dissociated. While for test group to which the drug was administered, the appearance of mitochondria was uniform, adventitia and spinal meninges system were clear to see, and the distribution of intact myofibril was uniform with every part being clearly distinguished. For the two groups administered with SMS and SMT, the mitochondria had an appearance of coacervation, and the damage was least.

SMS 11g/kg and SMT 22g/kg significantly improved body weight change and heart index at the seventh day after the mice were infected by virus. The content of IL-2 increased significantly. SMS 22g/kg increased activity of spleen NK cells significantly. The group administered with SMT 22g/kg had a tendency of increasing activity of NK cells. Here, both of them had a tendency of lowering IFN-γ which was too high in blood plasma.

TABLE 1

Effect of SMT on blood serum CK, LDH, AST activities after the mice were infected by Coxsackie virus $B_3$ 10 days

| Group | dosage (g/kg) | CK (u/L) | LDH (u/L) | AST (u/L) |
|---|---|---|---|---|
| Control | | 315.64 ± 112.16 | 2334.55 ± 355.41 | 42.89 ± 15.76 |
| SMS | 11 | 504.37 ± 184.34 | 2857.81 ± 494.36* | 233.59 ± 81.442 |

TABLE 1-continued

Effect of SMT on blood serum CK, LDH, AST activities after the mice were infected by Coxsackie virus $B_3$ 10 days

| Group | dosage (g/kg) | CK (u/L) | LDH (u/L) | AST (u/L) |
|---|---|---|---|---|
| SMT | 12 | 390.48 ± 99.86* | 2819.37 ± 421.83* | 108.27 ± 36.29* |
| Model | | 555.35 ± 192.42## | 3376.42 ± 457.51## | 154.55 ± 31.03## |

The above values were the average of 7~10 mice.

TABLE 2

Effect of SMT on myocardium and histo-pathological change after the mice were infected by Coxsackie virus $B_3$ 10 days.

| Group | | Control | SMS | SMT | Model |
|---|---|---|---|---|---|
| Dosage (g/kg) | | | 11 | 12 | |
| Number of animals | | 5 | 10 | 8 | 7 |
| Degree of necrosis | ± | 1 | 1 | 2 | 1 |
| | + | 0 | 5 | 6 | 0 |
| | ++ | 0 | 3 | 0 | 2 |
| | +++ | 0 | 1 | 0* | 3# |
| Degree of calcification | ± | 0 | 0 | 1 | 0 |
| | + | 0 | 3 | 0 | 0 |
| | ++ | 0 | 0 | 0 | 0 |
| | +++ | 0 | 2 | 0 | 2 |
| | ++++ | 0 | 0 | 0* | 0# |
| Degree of invasion | + | 0 | 4 | 6 | 2 |
| | ++ | 0 | 6 | 0* | 4## |

TABLE 3

Effect of SMT on body weight change and heart index after the mice were infected by Coxsackie virus $B_3$ 10 days.

| Group | Dosage (g/kg) | Increase of body weight (g) | Heart index (mg/10 g) |
|---|---|---|---|
| Control | | +0.14 ± 1.05 | 47.03 ± 4.93 |
| SMS | 22 | −3.36 ± 0.36* | 50.13 ± 1.87** |
| SMT | 22 | −4.03 ± 1.20 | 51.07 ± 1.63** |
| Model | | −4.62 ± 0.23## | 54.83 ± 1.99## |

The values listed above were the average of 8 mice.

TABLE 4

Effect of SMT on blood plasma Interleukin-2 and γ-Interferon contents and activity of spleen NK cells after the mice were infected by Coxsackie virus $B_3$ 7 days.

| Group | Dosage (g/kg) | Interleukin-2 (ng/ml) | γ-Interferon (pg/ml) | Activity of NK cells |
|---|---|---|---|---|
| Contrast | | 14.25 ± 3.74 | 74.07 ± 27.78 | 37.62 ± 15.91 |
| SMS | 22 | 14.09 ± 6.22* | 128.38 ± 17.66 | 30.65 ± 8.37* |
| SMT | 22 | 14.14 ± 4.53* | 122.13 ± 19.48 | 15.18 ± 4.60 |
| Model | | 8.70 ± 2.89## | 144.61 ± 33.68### | 10.25 ± 7.60# |

The above values were the average of 8 mice.
*$P < 0.05$ **$P < 0.01$, compared with control group
$P < 0.05$ ##$P <0.01$ ###$P <0.001$, compared with model group

What is claimed is:

1. A method for preparing a pharmaceutical composition for the treatment of cardiovascular diseases, the method comprising:

decocting in water a mixture of Radix Ginseng, Radix Ophiopogonis and Fructus Schisandrae Chinensis to obtain a water extract;

isolating polysaccharides, amino acids and saponin from the water extract, and mixing the isolated polysaccharides, amino acids and saponin to obtain the pharmaceutical composition, wherein the water extract is precipitated with an organic solvent selected from the group consisting of ethanol and acetone, to obtain the polysaccharides and a supernatant, which is adsorbed onto a macroporous adsorption resin;

the macroporous adsorption resin is eluted with ethanol and water to obtain an ethanol eluate and a water eluate;

the saponin is obtained by removing ethanol from the ethanol eluate;

the water eluate is adsorbed onto a cation exchange resin, which is then washed with water and then eluted with an ammonium solution to obtain an ammonium eluate; and the amino acids are obtained by drying the ammonium eluate.

2. A method for preparing a pharmaceutical composition for the treatment of cardiovascular diseases, the method comprising:

decocting in water a mixture of Radix Ginseng, Radix Ophiopogonis and Fructus Schisandrae Chinensis to obtain a water extract;

isolating polysaccharides, amino acids and saponin from the water extract, and mixing the isolated polysaccharides, amino acids and saponin to obtain the pharmaceutical composition, wherein the water extract is first adsorbed onto a cation exchange resin, which is eluted with water to obtain a first water eluate, and then eluted with an ammonium solution to obtain an ammonium eluate;

the amino acids are obtained by drying the ammonia eluate;

the first water eluate is adsorbed onto a macroporous adsorption resin, which is eluted with water to obtain a second water eluate, and then with ethanol to obtain an ethanol eluate;

the second water eluate is precipitated with ethanol to obtain the polysaccharides; and the saponin is obtained by removing ethanol from the ethanol eluate.

3. A method according to claim 1, wherein the organic solvent is ethanol.

4. A method accoridng to claim 1, wherein the ammonium solution has a concentration of about 2–15%.

5. A method accoridng to claim 1, wherein the ammonium solution has a concentration of about 2–15%.

6. A method according to claim 3, wherein the water extract is precipitated with a final ethanol concentration of 60–80%.

7. A method according to claim 2, wherein the second water eluate is precipitated with a final ethanol concentration of 60–80%.

8. A method according to claim 1, wherein the macroporous adsorption resin is eluted with ethanol having a concentration of about 70–80%.

9. A method according to claim 2, wherein the macroporous adsorption resin is eluted with ethanol having a concentration of about 70–80%.

* * * * *